(12) United States Patent
Jochum

(10) Patent No.: US 9,801,753 B2
(45) Date of Patent: Oct. 31, 2017

(54) VACUUM ATTACHMENT FOR A PENIS EXTENSION DEVICE

(71) Applicant: Herbert Jochum, Munsing (DE)

(72) Inventor: Herbert Jochum, Munsing (DE)

(73) Assignee: SWISS-TEC GLOBAL LTD., San Gwann (MT)

( * ) Notice: Subject to any disclaimer, the term of this patent is extended or adjusted under 35 U.S.C. 154(b) by 783 days.

(21) Appl. No.: 14/345,960

(22) PCT Filed: Sep. 21, 2012

(86) PCT No.: PCT/EP2012/068640
§ 371 (c)(1),
(2) Date: Dec. 30, 2014

(87) PCT Pub. No.: WO2013/041675
PCT Pub. Date: Mar. 28, 2013

(65) Prior Publication Data
US 2015/0105609 A1    Apr. 16, 2015

(30) Foreign Application Priority Data

Sep. 22, 2011    (EP) .................................... 11182330

(51) Int. Cl.
*A61F 5/00*    (2006.01)
*A61F 5/41*    (2006.01)

(52) U.S. Cl.
CPC .......... *A61F 5/41* (2013.01); *A61F 2005/412* (2013.01)

(58) Field of Classification Search
CPC ..... A61F 5/41; A61F 2005/412; A61H 19/00; A61H 19/30; A61H 19/32

USPC ...................................................... 600/38–41
See application file for complete search history.

(56) References Cited

FOREIGN PATENT DOCUMENTS

| DE | 8700174.8 | 4/1987 |
| DE | 102007017222 A1 | 12/2007 |
| WO | 2004004610 A1 | 1/2004 |
| WO | 2010094677 A1 | 8/2010 |

*Primary Examiner* — John Lacyk
(74) *Attorney, Agent, or Firm* — Bacon & Thomas, PLLC

(57) ABSTRACT

A connecting device is made available for connecting the distal part of a penis to a penis extension device, wherein the connecting device (1) has an elongate, rigid hollow body (3), which is open at the proximal end and is used for receiving the distal end of the penis and for securing on the penis extension device and, at its distal end, has an opening (31) that is in operational connection to a vacuum pump (4) or can be brought into such an operational connection, and an elastic tubular sleeve (2) which is placed with its proximal area (5) onto the shaft of the penis and which, when the connecting device (1) is in the assembled state, has its distal area (6) enclosing the proximal end of the hollow body (3) and bearing on the outside thereof. This connecting device is characterized in that the wall thickness of the sleeve (2) in the distal area (6) is greater than in the proximal area (5) and/or a three-way valve is arranged between the opening (31) and the vacuum pump (4) and can assume the following positions:
i) the interior of the hollow body (3) is connected to the environment,
ii) the opening (31) and therefore the hollow body (3) are closed, and
iii) the interior of the hollow body (3) is connected to the vacuum pump (4).

15 Claims, 8 Drawing Sheets

CROSS-SECTION A-A

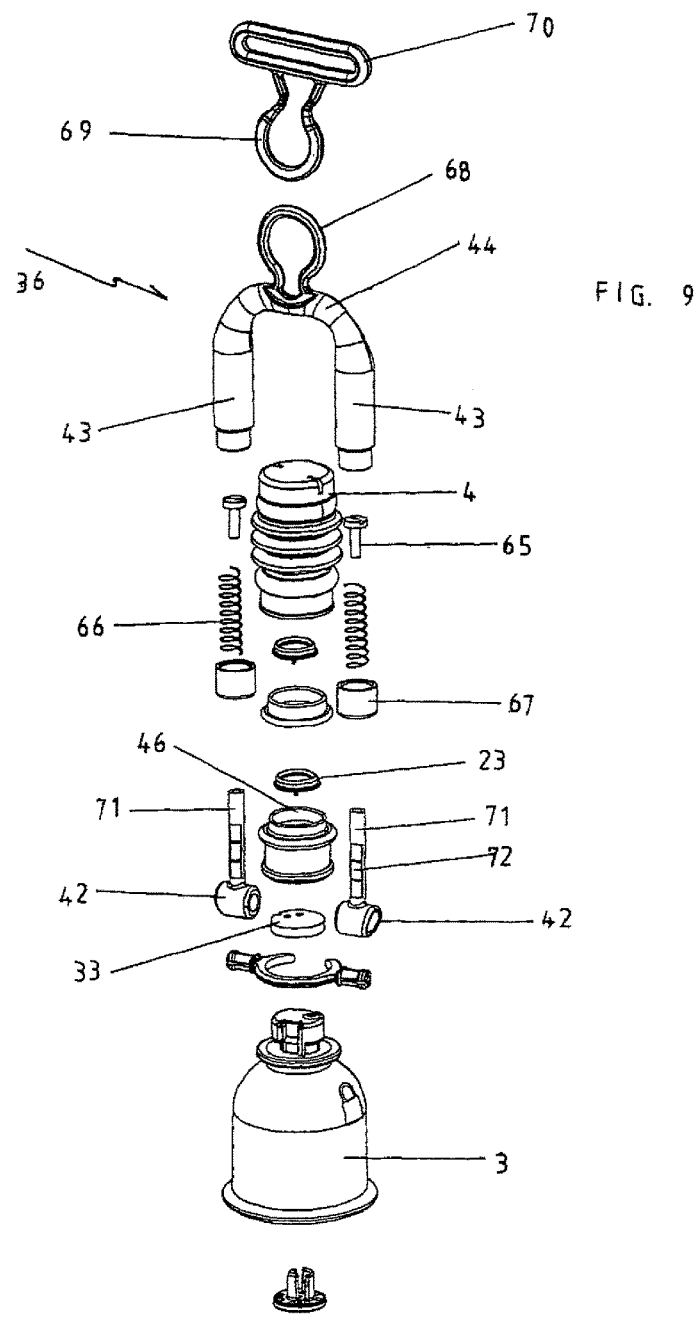

VACUUM ATTACHMENT FOR A PENIS EXTENSION DEVICE

Figure 1:
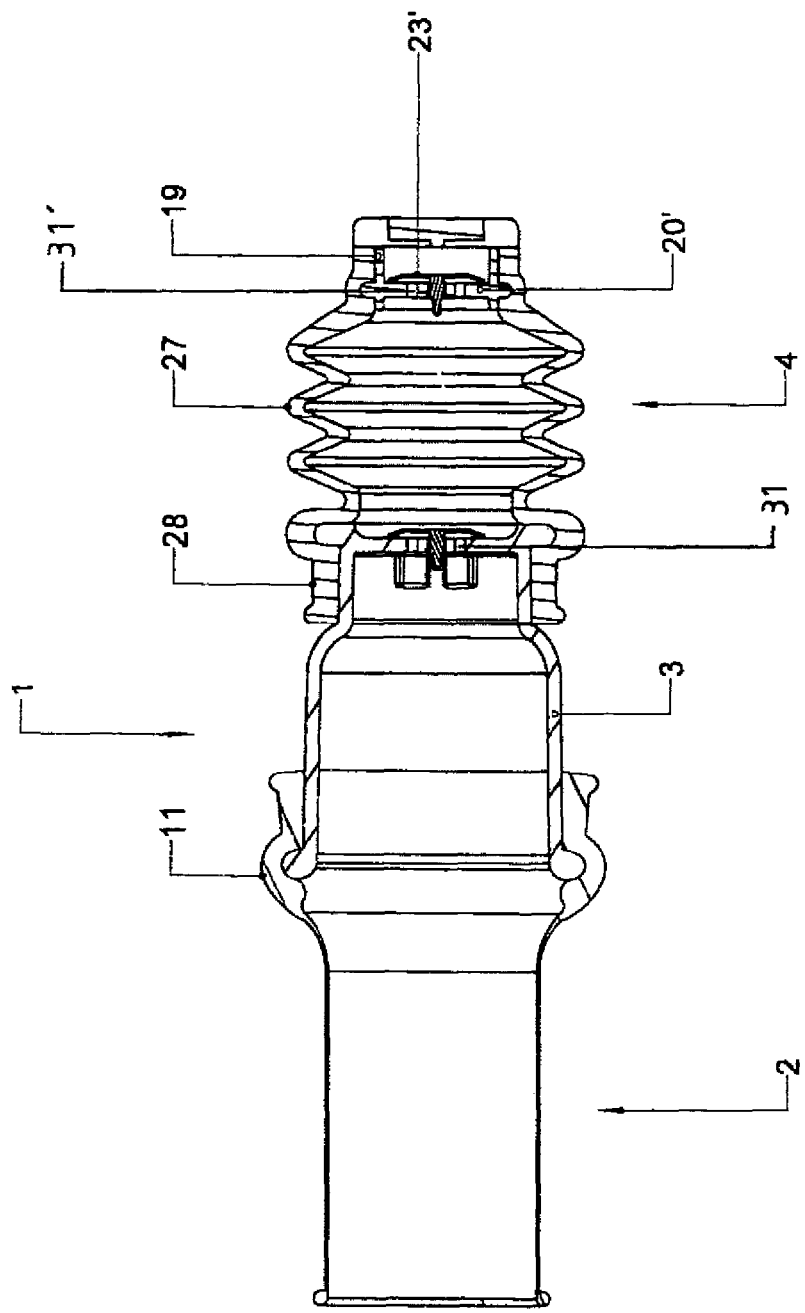

The invention relates to a connecting device for connecting the distal part of a penis to a penis extension device, wherein the connecting device has an elongate, rigid hollow body, which is open at the proximal end and is used for receiving the distal end of the penis and for securing on the penis extension device, and an elastic tubular sleeve which is placed with its proximal area onto the shaft of the penis and which, when the connecting device is in the assembled state, has its distal area enclosing the proximal end of the hollow body and bearing on the outside thereof.

Penis extension appliances or devices are known in a very wide variety of designs; see, for example, DE 100 01 331 A1, U.S. Pat. No. 5,707,341 and EP 1 779 822 A1.

What these appliances have in common is that a longer-acting pull is exerted on the penis, such that new tissue forms and leads to an enlargement of the penis. Certain diseases can also be treated using these devices. Hence, these devices are not erection aids or the like. Instead, a pull is exerted on the penis in the non-erect state.

For this purpose, it is necessary for the penis extension device to be connected to the penis so that this pull can be exerted. It goes without saying that the starting point for transmitting the pull should be at the distal end of the penis.

It has now been proposed to connect a penis extension device to the penis with the aid of a loop engaging behind the glans of the penis. Condoms and cylindrical hollow bodies have furthermore been proposed (U.S. Pat. No. 5,707,341 and EP 1 779 822 A1).

So-called glans cradles are known from DE 20 206 017 667 U1 and DE 20 207 003 824 U1, onto which the penis is placed and secured with the aid of a fixing element. The fixing element engages behind the glans, and thus on the proximal side of the glans, and prevents the penis from being pulled away from the support element when a pull is exerted.

A disadvantage of these known securing elements is that either they do not reliably fix the penis and/or they are awkward to put on.

The object of the invention is to make available a simply constructed connecting device of the type in question which is of simple construction and which ensures a reliable and also protective connection to the penis extension device.

This object is achieved by a connecting device according to the invention as claimed in claim 1.

The connecting device according to the invention is characterized in that the wall thickness of the sleeve in the distal area is greater than in the proximal area.

It is thus ensured that the sleeve in the proximal area is chosen in such a way that the sleeve, which represents a kind of condom, is sufficiently flexible in this area that comes to lie on the shaft of the penis. In the distal area, on account of the greater wall thickness, the sleeve has a sufficient inherent stability and load-bearing capacity to be able to take up the forces that are applied to the sleeve in this area. At the same time, however, it is still elastic enough to be able to be fitted onto the rigid hollow body. In addition, it largely maintains its intrinsic shape.

The wall thickness of the sleeve in the distal area is preferably 4 to 15 times as great as the wall thickness of the sleeve in the proximal area. With the expression "4 to 15 times as great", all values falling into this range are disclosed, in particular 4 times, 5 times, 6 times, 7 times, 8 times, 9 times, 10 times, 11 times, 1 times, 13 times, 14 times and 15 times as great.

Preferably, the wall thickness of the sleeve is 0.20 to 0.40 mm in the distal area and 2 to 5 mm in the distal area.

Said range of 0.20 to 0.40 mm for the wall thickness of the sleeve in the proximal area comprises all values lying in said range, for example 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39 and 0.40 mm. In particular, preferred values are 0.25, 0.30 and 0.35 mm.

Said range of 2 to 5 mm for the wall thickness of the sleeve in the distal area comprises all values falling into this range, for example 2.0, 2.5, 3.0, 3.5, 4.0, 4.5 and 5.0 mm. In particular, 2.5, 3.0 and 3.5 mm are preferred.

According to a preferred embodiment, the wall thickness of the sleeve decreases continuously at the transition from the distal area to the proximal area.

The hollow body can be of any desired cross-sectional shape. According to a further preferred embodiment, the hollow body is cylindrical and, at least in the proximal area, represents a kind of hollow cylindrical tube. It does not in this case have to be an exact cylinder; the cross-sectional shape of the hollow body can therefore be not only circular but also elliptic.

The distal area of the sleeve is preferably divided into a transition area to the proximal area and into an end area facing toward the hollow body. The sleeve is preferably cylindrical in the proximal area and in the area facing toward the hollow body and thus likewise represents a kind of hollow cylindrical tube. On account of the small wall thickness, the sleeve in the proximal area does not of course maintain its shape without support and instead "collapses", as is the case with conventional condoms. However, in the distal area, on account of the greater wall thickness, the sleeve has sufficient dimensional stability in order to largely maintain the cylindrical tube shape in the unsupported state.

The internal diameter of the sleeve relates to the hollow cylindrical state and is more or less the same in the proximal area and in the end area facing toward the hollow body. This relates to an unextended state of the various parts of the sleeve. The internal diameter of the sleeve in the transition area is preferably greater, as will be discussed in more detail below.

According to a further preferred embodiment, the hollow body, at its proximal edge, is equipped with a bead extending radially outward, or it forms such a bead. The sleeve extends radially outward like a bead in the transition area and has, in its inside wall, a circumferential groove of which the bottom points radially outward and which, as regards the cross section of the groove or of the bead, is designed with a surface and shape approximately congruent to the bead of the hollow body, in such a way that the bead of the hollow body can come to lie in the groove and remains there.

The hollow body is open at its distal end. In the simplest case, the hollow body can therefore be a kind of hollow cylindrical tube. The opening is preferably in operational connection to a vacuum pump. In this way, underpressure can be generated in the interior of the hollow body when the sleeve lies sealingly against the shaft of the penis and against the hollow body. Of course, suitable measures then have to be taken to ensure that this vacuum is maintained, for example by provision of a nonreturn valve. By means of this vacuum, the connecting device according to the invention remains more permanently connected to the shaft of the penis, even when a pull is applied to the connecting device according to the invention by a conventional penis extension appliance.

The tensile force to which the connecting device is subjected by the penis extension appliance can be exerted by a suitable coupling element, which is connected in any desired way to the hollow body.

The sleeve is preferably made from medical silicone. A very soft silicone is expediently used that has a 300 to 500 times extensibility.

The rigid hollow body is made from a suitable plastic and is expediently injection molded. According to the invention, a rigid hollow body is not to be understood as simply meaning hollow bodies that are not deformable at all. Instead, it also means hollow bodies which have a degree of deformability under pressure or tension but which nevertheless substantially maintain the shape given to them and therefore have sufficient dimensional stability.

The invention further relates to a connecting device as claimed in claim 6, by which the above-mentioned object is likewise achieved.

Accordingly, a three-way valve is arranged between the opening and the vacuum pump (the interior) and can assume the following positions:

a. The interior of the hollow body is connected to the environment; this represents the ventilation position.
b. The opening and therefore the hollow body are closed; this represents the closed position, and
c. the interior of the hollow body is connected to the vacuum pump (more precisely the interior of the vacuum pump); this represents the pumping position.

A connecting device of this kind can be equipped or combined with a sleeve of the kind described above or with a sleeve which more or less represents a conventional condom.

The three-way valve preferably has a rotatable sealing disk, in which at least one continuous opening is provided which is arranged off-center and can be brought into axial alignment with the opening by rotation of the sealing disk. This position represents the pumping position.

A further continuous opening is provided in the sealing disk, which continuous opening is likewise arranged off-center and can be brought into axial alignment with the opening by rotation of the sealing disk and is connected to the environment via a channel. This position is the ventilation position.

Moreover, the sealing disk can be rotated in such a way that the opening is closed. This position is the closed position.

Together with the vacuum pump, the three-way valve preferably forms, or elements of the three-way valve preferably form, an easily manageable unit that can also preferably be separated completely from the hollow body and can also be reconnected thereto.

The connecting devices equipped with the above-described embodiments of the three-way valve and the sealing disk can also cooperate with a sleeve according to the invention, as described in detail above, or with a conventional sleeve.

The invention also relates to a sleeve having the features of claim 1. Preferred embodiments of this sleeve are explained in more detail in the dependent claims and in the description given here.

Figure 2:
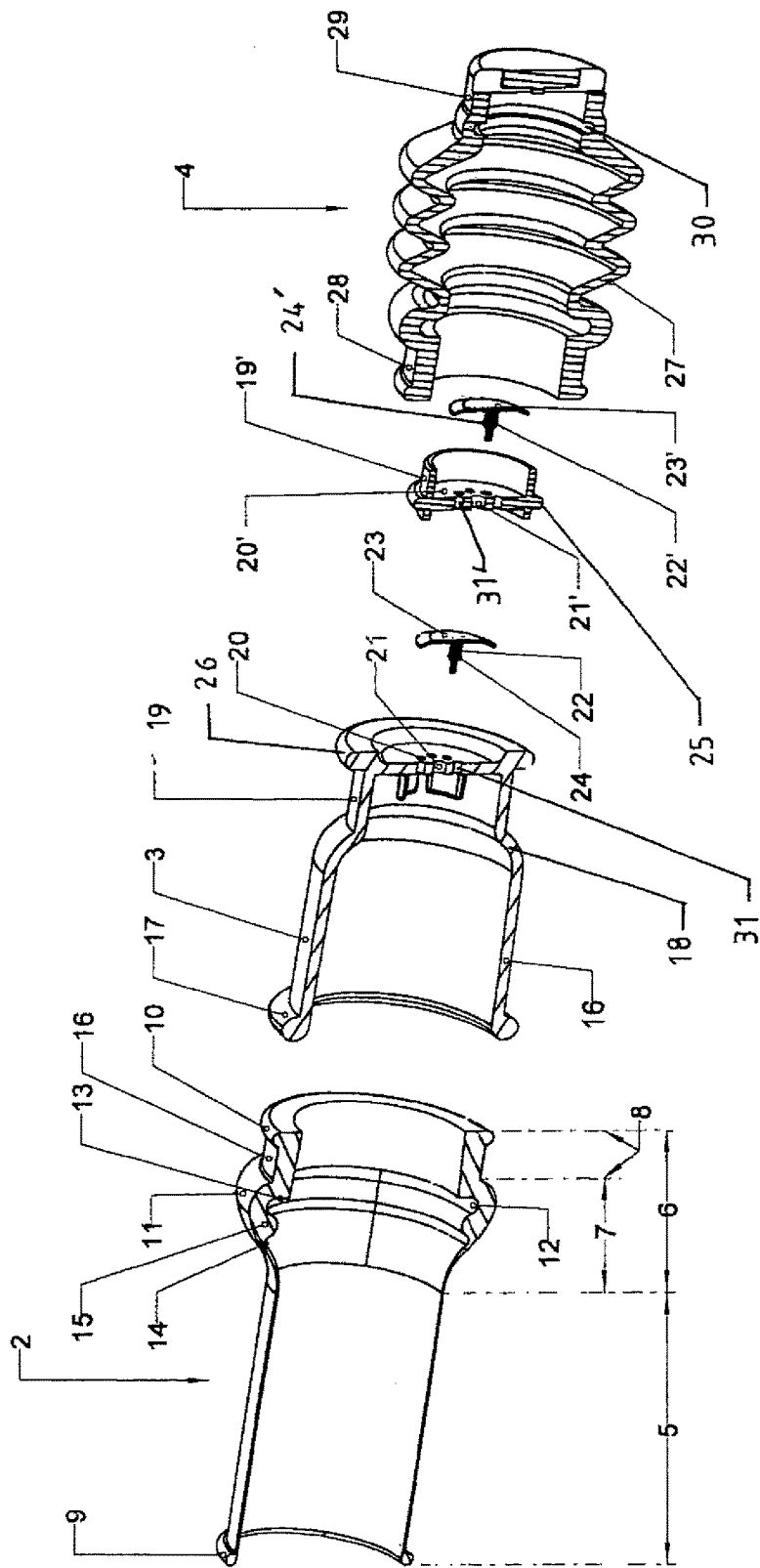
Figure 3:
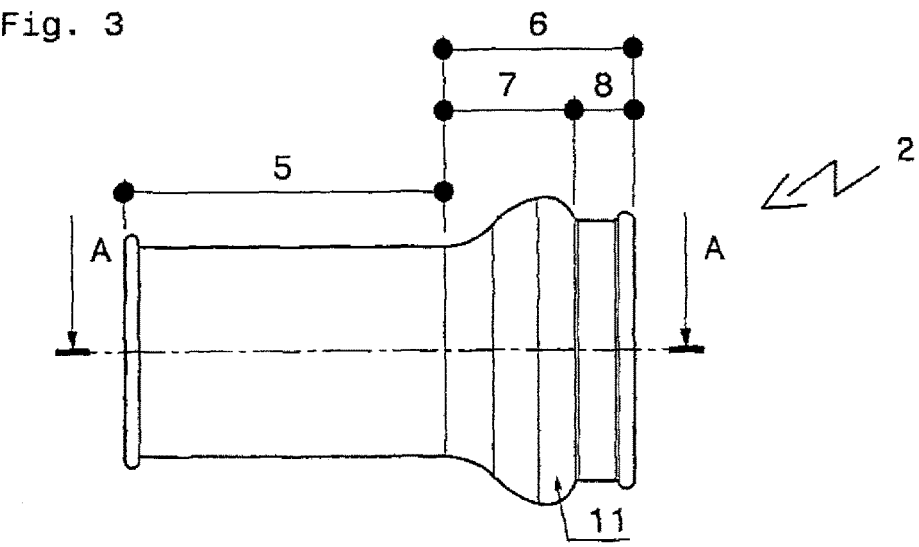
Figure 4:
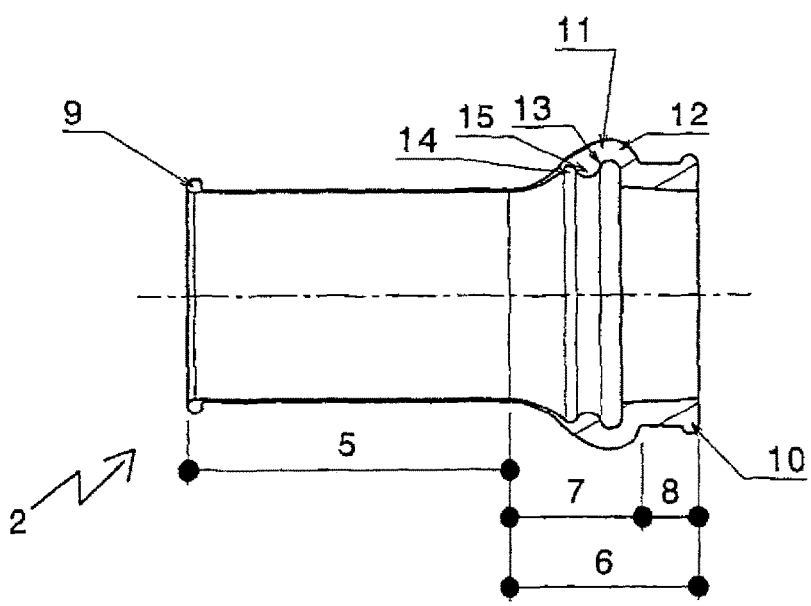
Figure 5:
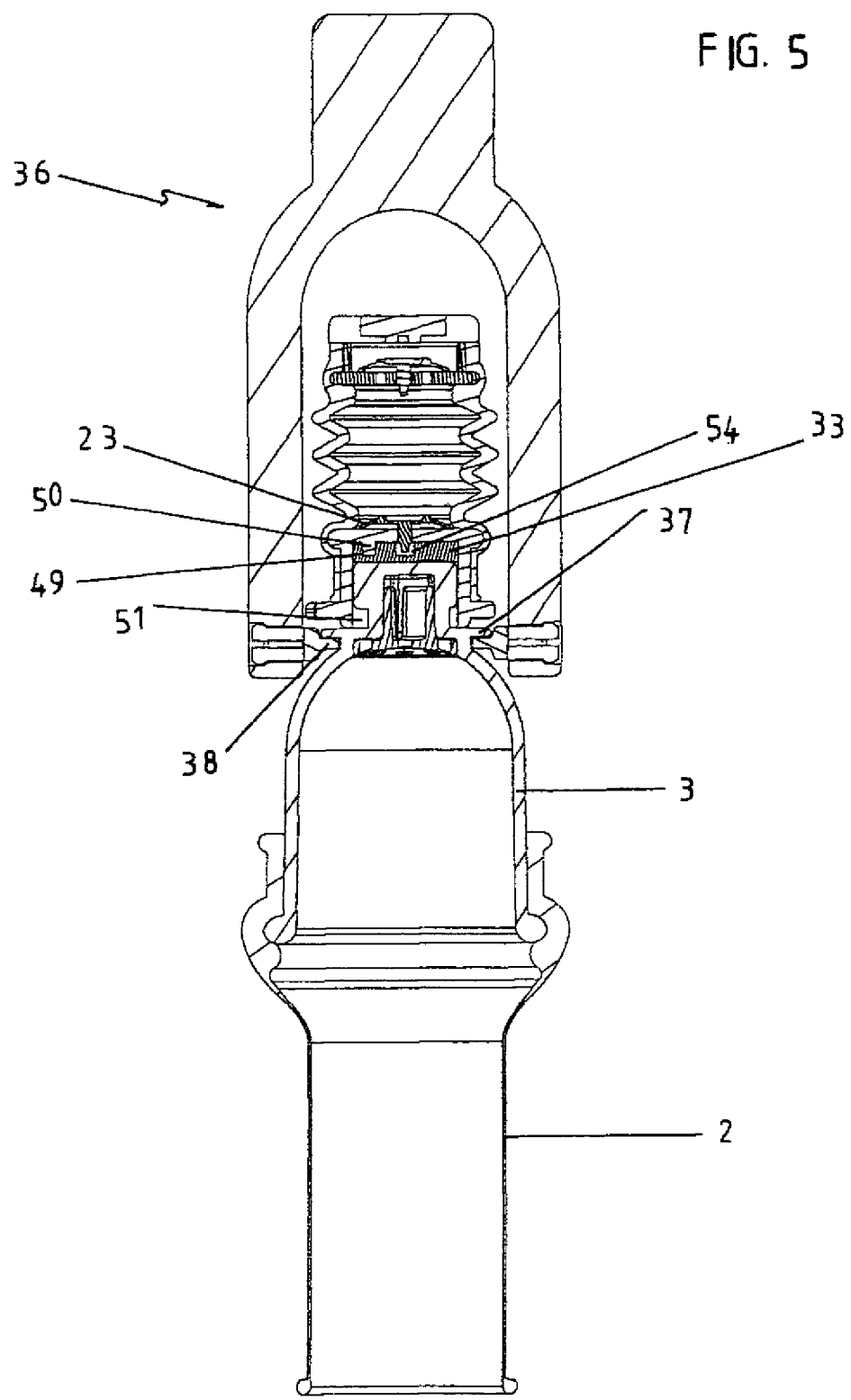
Figure 6:
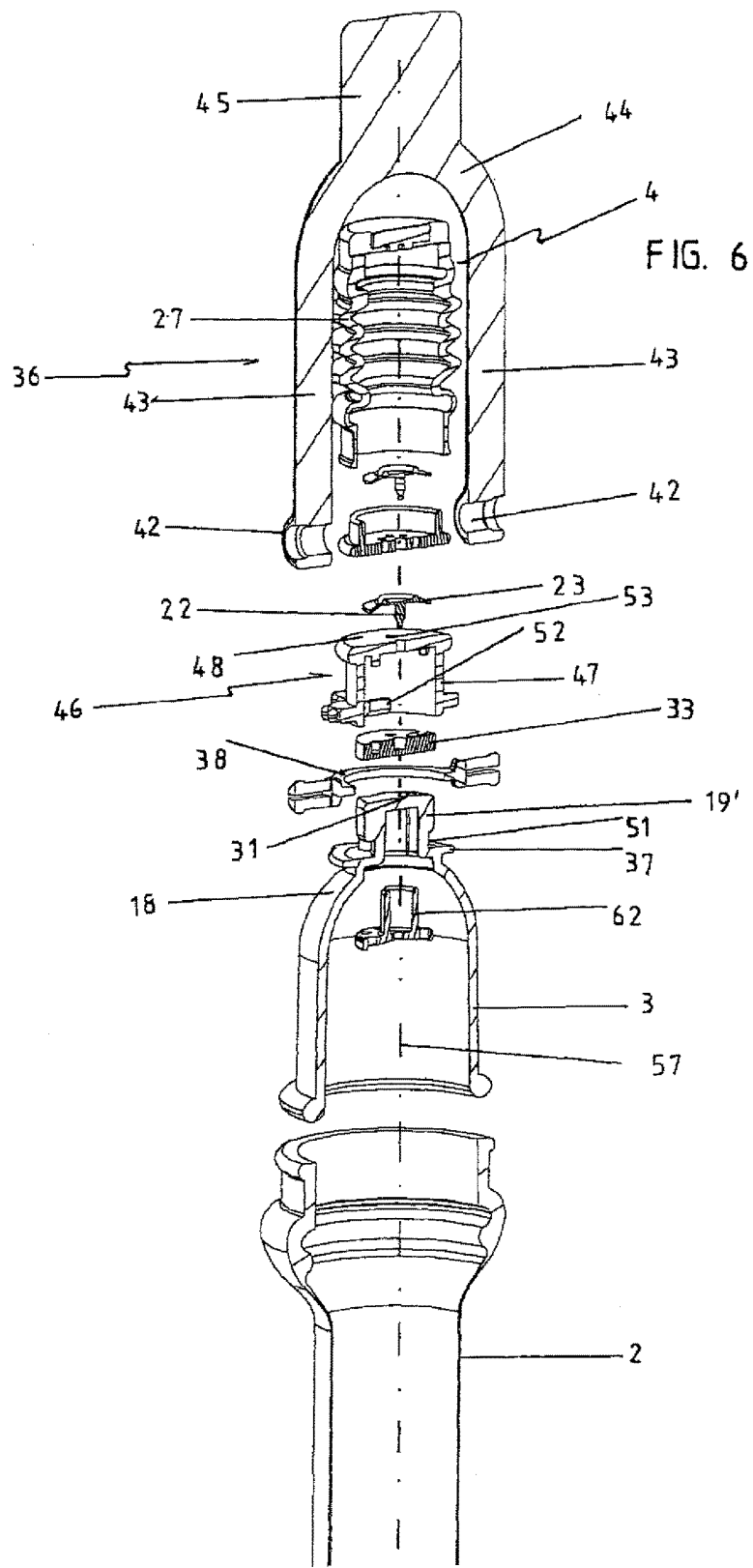
Figure 7:
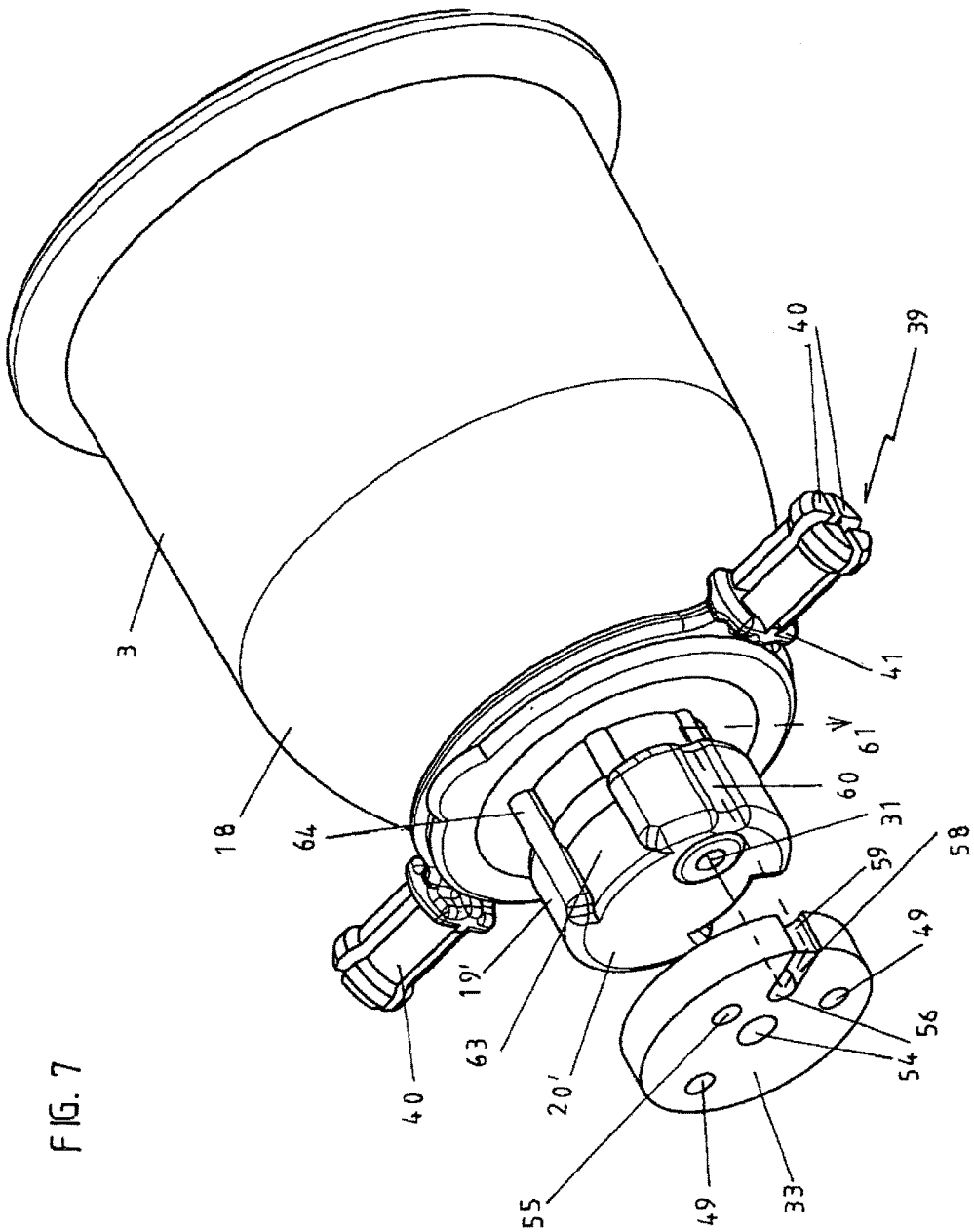
Figure 8:
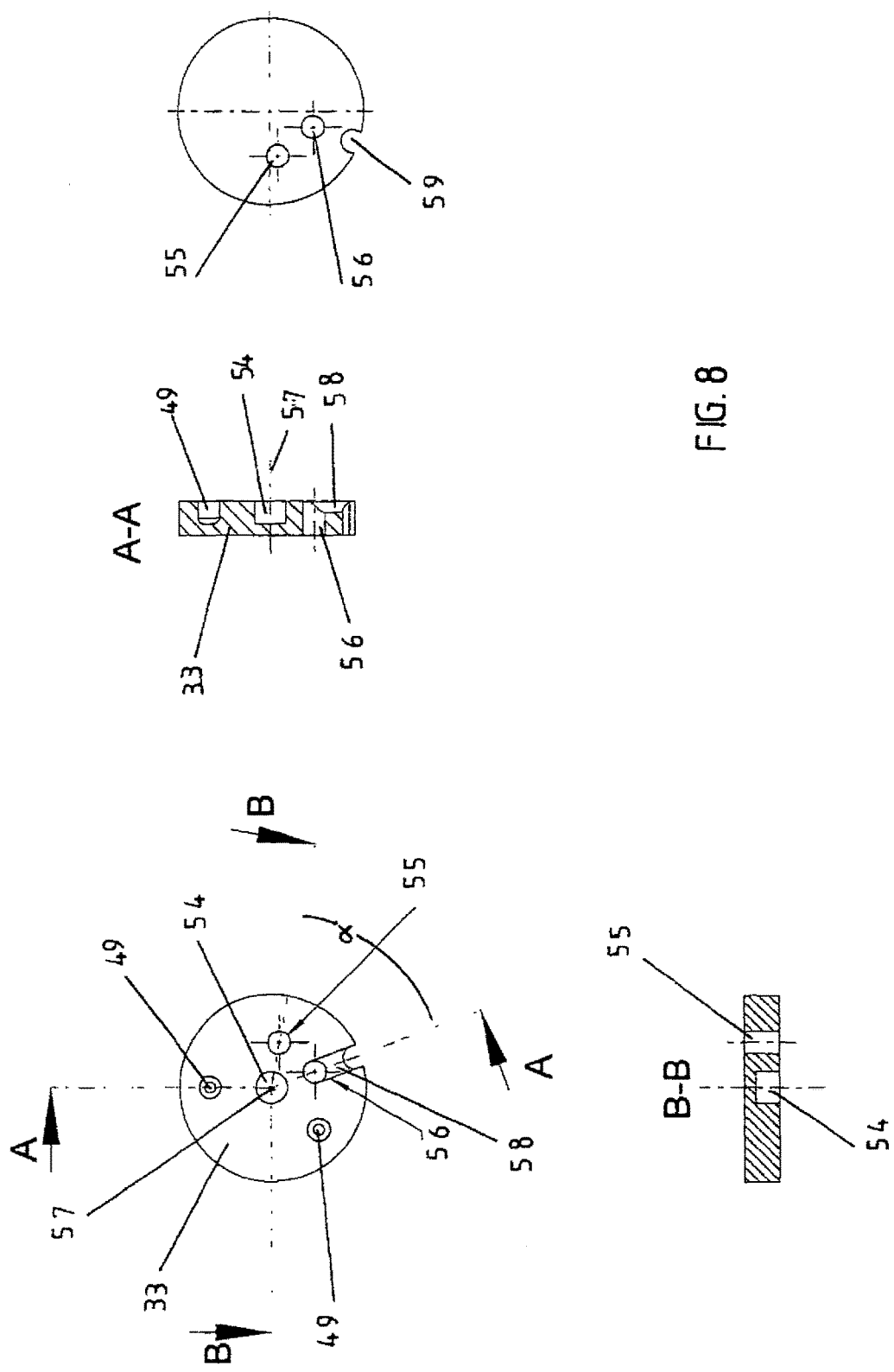

The invention is explained in more detail below with reference to diagrammatic drawings which are not true to scale and which show preferred embodiments. In these drawings:

FIG. 1 shows a cross-sectional view of a connecting device according to the invention with a sleeve according to the invention, a hollow body and a vacuum pump, FIG. 2 shows an exploded view of the connecting device shown in FIG. 1, FIG. 3 shows a side view of the sleeve of the connecting device shown in FIG. 1, FIG. 4 shows a cross-sectional view, along the lines A-A, of the sleeve shown in FIG. 3, FIG. 5 shows a longitudinal cross-sectional view of a further embodiment of a connecting device according to the invention, FIG. 6 shows the further embodiment from FIG. 5 in an exploded view and in longitudinal section, FIG. 7 shows a perspective view of the hollow body of the embodiment shown in FIG. 5 and additionally depicts a rotatable disk, which is an element of a three-way valve, FIG. 8 shows two plan views of the disk shown in FIG. 7, with two sections A-A and B-B, and FIG. 9 shows a further embodiment of a connecting device in an exploded view, but without a sleeve.

The connecting device 1 according to the invention shown in FIG. 1 has a sleeve 2, which is made from medical silicone and is connected to a rigid hollow body 3, which is in turn connected to a vacuum pump 4.

As can be seen in particular from FIGS. 2 and 4, the sleeve 2 has two areas, namely a proximal area 5 and a distal area 6. The distal area 6 is in turn divided into a transition area 7 to the proximal area 5 and into an end area 8 facing toward the hollow body 3.

As in the case of a normal condom, the proximal area 5 of the sleeve 2 comes to lie on the shaft of the penis. The proximal edge 9 is bead-like and thus contributes to the ability of the proximal area 5 to be rolled and unrolled. Typical diameter values for the proximal area 5, when the latter is of cylindrical form, are 20, 25 or 30 mm, for example.

The end area 8 of the distal area 6 of the sleeve 2 likewise has a radially outwardly extending bead 10. Proceeding from this bead 10, the end area 8 extends in a hollow cylindrical shape in the direction of the proximal area. The external diameter of this end area 8 remains approximately the same as far as the beginning of the transition area 7. The same applies to the internal diameter proceeding from the bead/edge 10 toward the transition area 7. The wall thickness of the end area 8 is approximately 3 mm.

In the transition area 7, the external diameter increases by a few millimeters, starting at the end area 8. Thereafter, the external diameter of the transition area 7 decreases again in the direction of the proximal area and corresponds, at the end of the transition area, to that of the proximal area 5. The sleeve 2 thus forms a radially outwardly extending bead 11 in the transition area 7.

In the portion in which the bead 11 has its greatest external diameter, a radially circumferential groove 12 is formed in the inside wall 13. The bottom of the groove 12 points radially outward. The internal diameter of the transition area 7 of the sleeve 2 in the area of this groove 12 is therefore greater than the internal diameter in the end area 8 and also greater than the internal diameter in the proximal area 5.

In the transition area 7, a second groove 14 is formed between the groove 12 and the proximal area 5. This second groove 14 also runs radially about the circumference; its bottom likewise points radially outward. Between the two grooves 12 and 14, a radially inwardly pointing circumferential bead 15 is formed in this construction.

Beginning at this bead 15, the wall thickness of the sleeve 2 decreases in the transition area 7, and it reduces in the proximal direction, beginning at the second groove 14, until it has reached the wall thickness of the sleeve 2 in the proximal area 5.

The internal diameter of the sleeve 2 is greater in the transition area 7 than in the areas adjoining the latter on both sides, namely the proximal area 5 and the end area 8. Between the bead 11 and the bead 10 at the distal edge, this end area 8 forms a kind of cylindrical tube segment. The external diameter of the sleeve 2 in the end area decreases slightly toward the bead 11.

The hollow body 3, which can be seen in particular from FIG. 2, has a proximal cylindrical tube portion 16, of which the proximal edge is designed as a radially outwardly extending bead 17. In the assembled state (see FIG. 1), this bead 17 comes to lie in the groove 12 in the transition area 7 of the sleeve 2. The end area 8 bears on the outer lateral surface of the cylindrical tube portion 16 of the hollow body 3. By means of the bead 17 engaging in the groove 12, it is possible only with difficulty for the sleeve 2, once it has been pushed with the end area 8 onto the hollow body 3, to be removed from the hollow body 3 by pulling them apart.

To apply the connecting device according to the invention, the sleeve 2 is rolled up in the direction of the hollow body starting from the edge 9. The rolled-up edge 9 is then finally pulled over the bead 11 in the transition area 7. Since the external diameter of the sleeve 2 in the end area 8 is smaller than in the transition area 7, the pulled-over edge remains between the bead 11 and the bead 10 at the distal edge of the end area 8.

In this state, the connecting device according to the invention is ready for use.

To connect the connecting device 1 to a penis, the rolled-up edge 9 is unrolled onto the shaft of an inserted penis (the glans being located inside the hollow body 3) in the reverse of the procedure described above.

At its distal end, the hollow body 3 is designed as a dome 18. At the top of the dome 18, the latter merges into a cylindrical tube portion 19, which is closed by a disk 20 with several openings, namely a central opening 21 and several off-centered or eccentric openings 31.

A cylindrical pin 22, which is connected axially on the outside to a flat flexible cap 23, is inserted into the central opening 21. This cap 23 constitutes a valve lid and is made from an elastic material, for example rubber. The pin 22 extends through the central opening 21. On the side of the disk 20 lying opposite the cap 23, the pin 22 has a radially outwardly projecting edge 24, which prevents a movement of the cap 23 or of the pin 22 in the distal direction. Together with the cap 23, the disk 20 forms a nonreturn valve; the air located in the interior of the hollow body 3 can only escape or travel outward axially in the distal direction and thus away from the hollow body 3 or out of the hollow body 3. The flexible cap 23 is lifted by the air stream, and the air can escape through the openings 31 and 21, which are arranged radially inward with respect to the outer edge of the cap 23. If the air moves in the reverse direction, the cap 23 closes the openings 21 and 31.

The described parts of this nonreturn valve are produced from suitable material and have the requisite flexibility to be able to perform their task.

At its distal end, the cylindrical tube portion 19 has a radially outwardly extending bead 26. In the assembled state, a vacuum pump 4 is fitted onto the cylindrical tube portion 19. This vacuum pump 4 has a cylindrical bellows 27. At its proximal end, the bellows 27 merges into a cylindrical tube portion 28 which, in the assembled state, bears externally around the cylindrical tube portion 19 of the hollow body 3.

The bellows 27 is produced from an elastic material, for example from a rubber-like material, such that it can be pressed together in the axial direction and expands again independently. At its distal end, the bellow 27 merges into an approximately hollow cylindrical portion 29, of which the internal diameter is smaller than the internal diameter of the hollow body 3 and also of the bellows 27. Inserted into this cylindrical portion 29 is a second nonreturn valve (see FIG. 1 in particular) which is basically designed in the same way as the nonreturn valve in the distal end of the hollow body 3 and is composed of a cylindrical tube portion 19', a disk 20', several openings 21' and 31', a cap 23', and a pin 22' with a projection 24'. This nonreturn valve is produced from the same material as the nonreturn valve at the distal end of the hollow body 3.

The cylindrical tube portion 19' has, radially on the outside, a circumferential bead 25 which, when the nonreturn valve is inserted into the hollow cylindrical portion 29, engages in a corresponding circumferential groove 30.

When the bellows 27 is pressed together in the axial direction and in the proximal direction, the nonreturn valve in the hollow cylindrical portion 29 opens, while the nonreturn valve in the hollow body 3 is closed, such that air escapes from the interior of the bellows 27. The area above or distally outside the cap 23' is connected to the environment or the atmosphere, for example via a channel (not shown).

By virtue of the inherent elasticity of the bellows 27, the latter expands again in the axial direction, and thus in the distal direction, and in this way generates a vacuum compared to the interior of the hollow body 3. As a result of the overpressure in the interior of the hollow body 3, the nonreturn valve located in this hollow body 3 is opened. Air flows in the direction of the interior of the bellows 27. The more often this pumping process is repeated, the greater the vacuum generated in the interior of the hollow body 3.

The interior of the bellows 27 is available as a reserve vacuum space. If, when the bellows 27 is compressed, air passes from the outside into the interior of the hollow body 3 and/or of the bellows 27, the vacuum is then basically maintained since and for as long as the bellows 27 can expand. Moreover, the user can repeat the above-described pumping process if necessary.

Of course, in addition to the described vacuum pump 4 with the bellows 27, other vacuum pumps known per se can also be connected to the hollow body 3 via the opening(s) 31; in this case too, the hollow body 3 is operationally connected to the vacuum pump via the opening(s) 31 as in the bellows 27. Moreover, other vacuum pumps can also be used which are connected in another way to the interior of the hollow body 3.

The coupling of the connecting device 1 according to the invention to a penis extension appliance (not shown) can be achieved in any desired manner. For this purpose, it is possible to use, for example, a loop, buckle or the like that engages on the cylindrical tube portion 28 or 19 and exerts a pull on the connecting device 1 according to the invention, in the direction of the penis extension appliance.

A coupling element 36, which is shown in FIGS. 5 and 6, is preferably used for this purpose. Although FIGS. 5 and 6 show a further embodiment of the connecting device 1 according to the invention as per FIGS. 1-4, this coupling element 36 can nevertheless also be used in the embodiment shown in FIGS. 1-4.

In FIGS. 5-8, moreover, reference signs for elements which are also already realized in the embodiment shown in FIGS. 1-4 are provided with the same reference signs.

To connect the hollow body 3 to the coupling element 36, an outward radially circumferential collar 37 is provided on the distal end of the hollow body 3 and is engaged from behind by a ring 38. This ring 38 is not closed but open, such that it can be placed axially in the proximal direction onto the hollow body with elastic widening and can engage behind said collar 37.

The ring 38 is provided with two radially extending pegs 39 which, lying diametrically opposite each other, are connected to or formed in one piece with the ring 38. These pegs 39 extend radially outward and therefore perpendicularly with respect to the longitudinal axis 57 of the connecting device 1. These pegs 39 have four peg elements 40, which are connected to a radially inwardly lying base 41. The four peg elements 40 of a peg 39 are spaced apart from one another and, together with the cavities or spaces lying between them, form a kind of cylindrical bolt which, as a result of the spaces between the peg elements 40, can nevertheless be pressed together.

A bearing bush 42 of a bow arm 43 is in each case pushed onto the two pegs 39. The pegs 39 protrude into the associated interior of the bearing bush 42 and result in a rotatable bearing of the bow arms 43.

The pegs 39 are also thickened radially to the outside. These thickened areas come to lie in a radially outwardly lying recess in the bearing bushes 42 and thus ensure that the bow arms 43 or the bearing bushes 42 can be pulled away from the pegs 39 only when force is applied in the radial direction and thus in the direction of the pegs 39.

The bow arms 43 extend in the distal direction parallel to the bellows 27 and to the vacuum pump 4 and, at their distal end, are connected to each other by an arch 44. This results in an approximately U-shaped element, which is pivotable in such a way that, during the pivoting movement, the vacuum pump 4 as it were swings through the opening outlined by the U shape.

At the distal end of the arch 44, an arrangement 45 is provided by means of which a connection to a penis extension device can be established. In the embodiment shown, this arrangement 45 is in the form of a clip which can be inserted into a socket and locked. Arrangements of this kind are known. The bow arms 43, together with the arch 44 and the bearing bushes 42, together form a kind of coupling element 36.

In the embodiment shown, the bow arms 43 are strip-like bow arms. However, the cross-sectional profile of the bow arms 43 can be of any desired kind and in particular can be elliptic.

A tension-measuring device can be built into one bow arm or into both bow arms 43 and, when the connecting device is placed on the penis and is additionally tensioned by the penis extension device, indicates the exerted tensile force to the user, for example by means of color markings. A tension-measuring device of this kind can be a spring balance, for example. A preferred tension-measuring device is explained in more detail below in connection with FIG. 9.

The hollow body 3 in the embodiment shown in FIGS. 5-8 is designed as a dome 18 at its distal end, in the same way as in the embodiment shown in FIGS. 1-4. This dome 18 continues in the distal direction in the form of a cylindrical tube portion 19', which is closed by a disk 20' forming a kind of lid. A continuous off-centered opening 31 or bore is provided in this lid. A pot-shaped attachment 46 with a cylindrically circumferential side wall 47 and with a bottom 48 is pushed onto this cylindrical tube portion 19'. A circular expandable sealing disk 33 made of an elastic or rubber-like material lies between the bottom 48 and the disk 20'.

On its distal side (upward in FIGS. 5 and 6), the rotatable sealing disk 33 has several blind holes 49 into each of which there engages a peg 50, which extends axially in the proximal direction (downward in FIGS. 5 and 6) from the proximal side of the bottom 48. This ensures that the sealing disk 33 is rotated when the pot-shaped attachment 46 is rotated. The sealing disk 33 bears with its radial side wall on the opposite inner lateral surface of the pot-shaped attachment 46.

In order to ensure that the pot-shaped attachment 46 is rotatable with respect to the cylindrical tube portion 19', two projections 52 lying radially opposite each other and extending radially inward are provided on the inner face of the side wall 47 of the pot-shaped attachment 46 and engage in a radially extending groove 51 at the proximal end of the cylindrical tube portion 19'. It is also possible for only one such projection to be provided. During the rotation of the pot-shaped attachment 46, the projections 52 slide along this groove 51. The sealing disk 33, which bears distally (upward in the figures) on the disk or the lid 20', is of course also carried along and rotated in the rotation of the pot-shaped attachment 46.

In order to be able to push the attachment 46 onto the cylindrical tube portion 19' from above, two axially extending grooves 63 are formed on the outside of the cylindrical tube portion 19'. When the attachment is being fitted in place, the projections 52 are rotated until they are able to slide axially along these grooves 53. As soon as the projections are located at the axial height of the radial groove 51, the attachment 46 can be rotated in relation to the cylindrical tube portion 19' and can then no longer be pulled off in the axial direction. If the attachment is to be pulled off again, it is rotated to a position in which the projections 52 are oriented axially with respect to groove 63. In order to ensure that a rotation can take place only in one direction, an edge of the axial groove 63 in the area of the radially extending groove 51 continues in the form of an axial web 64.

In the bottom 53, a continuous central bore 48 is provided through which a pin 22 of a cap 23 extends into a central blind hole 54 in the sealing disk 33. This cap 23 and the pin 22 are designed as in the embodiment described in FIGS. 1-4.

The pot-shaped attachment 46 with the associated bottom 48 and the cap 22 constitutes a first nonreturn valve, which corresponds approximately to the first nonreturn valve of the embodiment shown in FIGS. 1-4. This nonreturn valve is connected to a bellows 27 and thus to a vacuum pump 4. The vacuum pump 4 is otherwise also designed like the vacuum pump 4 of the embodiment shown in FIGS. 1-4. Moreover, the second nonreturn valve, which is present in this vacuum pump 4, is also constructed in the same way, such that further discussion is superfluous and is dispensed with for reasons of better clarity. The same applies to the reference signs.

By rotating the bellows 27, the pot-shaped attachment 46 and the sealing disk 33 are thus also rotated.

The sealing disk 33 also has a continuous off-centered bore 55 and a further off-centered continuous ventilation bore 56. The bore 55 and the ventilation bore 56 are at a distance in the radial direction from the center point of the sealing disk 33. The radial distance to the center of the sealing disk 33 is identical. This radial distance corresponds to the radial distance of the bore 31 in the disk 20'. In other words, the distance from the longitudinal axis 57 to the bores 31, 55 and 56 is the same.

The angle α enclosed by the radius from the longitudinal axis 57 to the off-centered bore 55 and by the radius from the longitudinal axis 57 to the off-centered ventilation bore 56 in the sealing disk 33 is ca. 60°. This angle α is enclosed between the section lines A and B in the view shown at the top left of FIG. 8.

By rotating the sealing disk 33, either the bore 55 or the ventilation bore 56 can be brought into axial alignment with the bore 31.

When the bore 55 is in axial alignment with the bore 31 and therefore located over the latter, a continuous channel is formed from the interior of the hollow body 3 to the interior of the bellows 27 and thus of the vacuum pump 4. This position represents the pumping position, in which air is pumped out of the hollow body 3 when the bellows 27 or the vacuum pump 4 is actuated.

When the ventilation bore 56 is in axial alignment with the bore 31, this corresponds to the ventilation position, in which the interior of the hollow body 3 is connected to the environment and thus to the atmosphere.

In order to ensure such a connection, a channel 58 extends in the radial direction from the distal side of the ventilation bore 56 (see in particular the section A-A of FIG. 8).

Radially toward the outside, the radially outwardly extending channel 58 merges into an axially extending groove 59, which is open radially to the outside and extends along the entire height of the sealing disk 33 (see also FIG. 7).

When the ventilation bore 56 is in axial alignment with the opening 31 and is therefore located directly over the latter, a groove 60 is located underneath the sealing disk 33, and thus in the proximal direction, which groove 60 is formed in the outer wall of the cylindrical tube portion 19 and extends in the axial direction. The groove 60 is thus open to the environment and the open air. The route which leads to the open air, and via which the interior of the hollow body 3 is thus connected to the outside (as regards this ventilation position), is indicated by an arrow 61 in FIG. 7.

If the sealing disk 33 is rotated in such a way that neither the bore 55 nor the ventilation bore 56 lies above the bore 31, this bore 31 is then closed. This closed position is chosen after the desired vacuum has been reached in the interior of the hollow body 3 with the aid of the vacuum pump 4. At the end of the pumping process, the sealing disk 33 is then simply rotated to this closed position. The interior of the vacuum pump 4 is then, like the bellows 27, also no longer in contact with the interior of the hollow body 3.

A sieve-like insert 62 is inserted into the interior of the cylindrical tube portion 19' and serves to protect the tip of the penis. This insert can be made from a soft material, but also from a rigid plastic.

The connecting device shown in an exploded view in FIG. 9 corresponds in many respects to the connecting device shown in FIG. 6. Identical parts or elements are therefore also provided with the same reference signs. In the connecting device shown in FIG. 9, the hollow body 3, the vacuum pump 4 and the pot-shaped attachment 46 with the associated rotatable sealing disk 33 are designed in the same way as in the connecting device shown in FIG. 6 and are also provided with the same reference signs.

In the connecting device shown in FIG. 9, the difference lies in the arrangement 45 by means of which a connection to a penis extension device (not shown) can be established.

The arrangement 45 in the embodiment shown in FIG. 9 has an arch 44, and two bow arms 43 which extend parallel to each other and are hollow on the inside. A cap 67 is in each case fitted or screwed onto the free ends of each of these hollow bow arms 43. Although these caps 67 therefore constitute the closure of the hollow bow arms 43, they are provided with a central bore (not shown) through which a respective hollow cylindrical pin 71 extends from the outside inward. A threaded screw 65 and a spring 66 are arranged in the interior of each of the bow arms 43. The threaded pin of this threaded screw 65 protrudes into the spring; one end of the spring 66 is supported on the head of the threaded screw 65, while the other end of the spring 66 is supported on the bottom of the cap 67. In their bottom, the caps 67 each have a bore through which the hollow cylindrical pin 71 extends from the outside inward and into the spring 66.

The threaded pin of the threaded screw 65 is screwed into the associated hollow cylindrical pin 71 which, for this purpose, has a corresponding thread.

In the assembled state, the hollow cylindrical pin 71 protrudes into the associated bow arm 43 and is not visible from the outside. In other words, the bearing bush 42 rests on the free end of the bow arm 43. When a tensile force is applied to the coupling element 36, the hollow cylindrical pin 71 is pulled to a greater or lesser extent out of the bow arm 43. On the outside of the hollow cylindrical pin 71 there is a marking 72, which has three areas of different colors. The greater the tensile force applied, the farther the hollow cylindrical pin 71 is pulled out from the bow arm 43 counter to the force of the spring 66. The more this bow arm 43 is pulled out, the more of the marking 72 is also visible from the outside. The tensile force applied is indicated in this way.

To connect the coupling element 36 to a penis extension appliance via a strap or the like, use is made of a ring element 68 which is secured on the arch 44 and which can cooperate with a ring element 69 of a buckle 70, which can be connected to a strap (not shown), in order to produce a connection. Such ring elements are known.

To ensure that the caps 67 can be firmly connected to the associated bow arms 43, the inner face of the circumferential side wall of the caps 67 is equipped with a thread, which cooperates with an outer thread on the free ends of the bow arms 43.

LIST OF REFERENCE SIGNS 1 connecting device
2 sleeve
3 hollow body
4 vacuum pump
5 proximal area of sleeve 2
6 distal area of sleeve 2
7 transition area of distal area 6
8 end area of distal area 6
9 proximal edge of proximal area 5
10 bead on distal edge of end area
11 bead in transition area 7 of distal area 6
12 groove
13 inside wall in transition area 7
14 second groove
15 inner bead
16 proximal cylindrical tube portion in end area
17 bead of hollow body 3
18 dome
19 cylindrical tube portion
20, 20' disk
21, 21' opening
22, 22' pin
23, 23' cap
24, 24' projection
25 bead
26 bead
27 bellows 28 cylindrical tube portion
29 cylindrical portion
30 groove
31, 31' off-centered opening/bore
32 continuous opening
33 rotatable sealing disk
34 further continuous opening
35 channel
36 coupling element
37 collar
38 ring
39 peg
40 peg element
41 base
42 bearing bush
43 bow arm
44 arch
45 arrangement
46 pot-shaped attachment
47 side wall of attachment 46
48 bottom of attachment 46
49 blind hole in sealing disk 33
50 peg at bottom 48
51 groove
52 projection
53 continuous bore in bottom 48
54 central blind hole in sealing disk 33
55 continuous off-centered bore in sealing disk 33
56 off-centered ventilation opening of sealing disk 33
57 longitudinal axis
58 channel
59 groove in sealing disk 33
60 groove in cylindrical tube portion 19'
61 arrow
62 sieve-like insert
63 axial groove
64 axial web
65 screw
66 spring
67 cap
68 ring element
69 ring element
70 buckle
71 hollow cylindrical pin
72 marking

The invention claimed is:

1. A connecting device configured to connect a distal part of a penis to a penis extension device, wherein the connecting device (1) has an elongate, rigid hollow body (3), which is open at a proximal end and is configured to receive a distal end of the penis and configured to be secured on the penis extension device and, at a distal end, has an opening (31) that is configured to be connected to a vacuum pump (4) or configured to be brought into such connection,
  and an elastic tubular sleeve (2) which is configured to be placed with a proximal area (5) onto a shaft of the penis and which, when the connecting device (1) is in the assembled state, has a distal area (6) enclosing the proximal end of the hollow body (3) and bearing on the outside thereof,
  further comprising:
  a three-way valve arranged between the opening (31) and the vacuum pump (4) and is able to assume the following positions:
  i) the interior of the hollow body (3) is connected to the environment,
  ii) the opening (31) and therefore the hollow body (3) are closed, and
  iii) the interior of the hollow body (3) is connected to the vacuum pump (4).

2. The connecting device as claimed in claim 1, wherein the three-way valve comprises a rotatable sealing disk (33), in which at least one continuous opening (32) is provided which is arranged off-center and is able to be brought into alignment with the opening (31) by rotation of the sealing disk, and
  a further continuous opening (34) is provided in the sealing disk (33), which continuous opening (34) is arranged off-center and is able to be brought into axial alignment with the opening (31) by rotation of the sealing disk (33) and is connected to the environment via a channel (58), and wherein the sealing disk (33) is able to be rotated in such a way that the opening (31) is closed.

3. The connecting device as claimed in claim 1, wherein the sleeve (2) is made from medical silicone.

4. The connecting device as claimed in one of the preceding claims, wherein the hollow body (3) is cylindrical, the distal area (6) of the sleeve (2) is divided into a transition area (7) to the proximal area (5) and into an end area (8) facing toward the hollow body (3), the sleeve (2) is cylindrical in the proximal area (5) and in the end area (8) facing toward the hollow body (3), and the internal diameter of the sleeve (2) in the proximal area (5) and in the end area (8) facing toward the hollow body (3) is more or less the same.

5. The connecting device as claimed in claim 4, wherein the hollow body (3), at a proximal edge, has a bead (17) extending radially outward, the sleeve (2) extends radially outward like a bead (11) in the transition area (7) and has, in an inside wall (13), a circumferential groove (12) which is designed with a surface and shape approximately congruent to the bead (17) of the hollow body.

6. The connecting device as claimed in claim 5, wherein the distal end of the hollow body (3) is dome-shaped (18), and the opening (31) is arranged in the dome (18).

7. The connecting device as claimed in claim 6, wherein the hollow body (3) has, at the distal end, a coupling element (36) via which the penis extension device is able transmit a tensile force to the connecting device (1).

8. The connecting device as claimed in claim 7, wherein the coupling element (36) is secured and mounted on the hollow body (3) so as to be movable and pivotable.

9. An elastic tubular sleeve configured to be coupled to a connecting device, comprising a proximal area which is configured to be placed with the proximal area (5) onto the shaft of a penis, wherein a wall thickness of the sleeve (2) being greater in a distal area (6) than in the proximal area (5), wherein the wall thickness of the sleeve (2) in the distal area (6) is 4 to 15 times as great as the wall thickness of the sleeve (2) in the proximal area (5).

10. The sleeve as claimed in claim 9, wherein the wall thickness of the sleeve (2) is 0.20 to 0.40 mm in the proximal area (5) and 2 to 5 mm in the distal area (6).

11. The sleeve as claimed in claim 9, wherein the wall thickness of the sleeve (2) decreases continuously at the transition from the distal area (6) to the proximal area (5).

12. The sleeve as claimed in claim 9, wherein the distal area (6) of the sleeve (2) is divided into a transition area (7) to the proximal area (5) and into an end area (8) facing toward the hollow body (3), the sleeve (2) is cylindrical in the proximal area (5) and in the end area (8) facing toward the hollow body (3), and the internal diameter of the sleeve (2) in the proximal area (5) and in the end area (8) facing toward the hollow body (3) is more or less the same.

13. The sleeve as claimed in claim 9, wherein the sleeve (2) extends radially outward like a bead (11) in the transition area (7) and has, in an inside wall (13), a circumferential groove (12) which is designed with a surface and shape approximately congruent to the bead (17) of the hollow body (3).

14. The sleeve as claimed in claim 9, wherein the sleeve (2) is made from medical silicone.

15. An elongate, rigid hollow body (3) for a connecting device configured to connect a distal part of a penis to a penis extension device wherein the hollow body is open at the proximal end, is configured to receive the distal part of the penis and configured to be secured on the penis extension device and, at a distal end, has an opening (31) that is configured to be connected to a vacuum pump (4) or configured to be brought into such connection, further comprising a three-way valve is arranged between the opening (31) and the vacuum pump (4) and is able assume the following positions:

i) the interior of the hollow body (3) is connected to the environment, ii) the opening (31) and therefore the hollow body (3) are closed, and iii) the interior of the hollow body (3) is connected to the vacuum pump (4).

\* \* \* \* \*